United States Patent [19]

Drake

[11] 4,322,315
[45] Mar. 30, 1982

[54] REGENERATION OF A RUTHENIUM CONTAINING HYDROGENATION CATALYST

[75] Inventor: Charles A. Drake, Bartlesville, Okla.

[73] Assignee: Phillips Petroleum Company, Bartlesville, Okla.

[21] Appl. No.: 143,670

[22] Filed: Apr. 25, 1980

[51] Int. Cl.³ .................. B01J 21/20; B01J 23/96; C07C 85/12
[52] U.S. Cl. .................... 252/415; 252/414; 564/491
[58] Field of Search ............. 252/411 R, 411 S, 414, 252/415, 412

[56] References Cited

U.S. PATENT DOCUMENTS

| | | | |
|---|---|---|---|
| 1,933,508 | 10/1933 | Peck | 252/414 |
| 3,177,158 | 4/1965 | Gleim | 252/414 |
| 3,419,503 | 12/1968 | Giannetti et al. | 252/411 R |
| 3,449,264 | 6/1969 | Myers | 252/441 |
| 3,480,558 | 11/1969 | Lum et al. | 252/416 |
| 3,625,860 | 12/1971 | Condrasky et al. | 252/415 |
| 3,896,174 | 7/1975 | Drake | 260/583 P |
| 4,053,515 | 10/1977 | Drake | 260/583 P |

OTHER PUBLICATIONS

"Catalytic Hydrogenation Over Platinum Metals", P. N. Rylander—Academic Press, 1967, N.Y., pp. 13-15.

*Primary Examiner*—P. E. Konopka

[57] ABSTRACT

A used ruthenium hydrogenation catalyst is regenerated by contact with carbon tetrachloride at a temperature in the approximate range of from about 0° to about 200° C. The carbon tetrachloride can be in liquid, gaseous or partly gaseous state.

13 Claims, No Drawings

REGENERATION OF A RUTHENIUM CONTAINING HYDROGENATION CATALYST

BRIEF SUMMARY OF THE INVENTION

A supported ruthenium catalyst which has been used for a hydrogenation reaction is regenerated by contacting the same with carbon tetrachloride which can be in liquid or gaseous state and at a temperature in the approximate range of from about 0° to about 200° C.

DETAILED DESCRIPTION

This invention relates to the regeneration of a used ruthenium hydrogenation catalyst. In one of its aspects, it relates to a relatively low temperature of regeneration of such a used catalyst. In a further aspect of the invention, it relates to the use of an organic solvent during the regeneration.

In one of its concepts the invention provides a process for the regeneration of a used ruthenium-containing, supported hydrogenation catalyst by treating the catalyst with carbon tetrachloride. In a further concept of the invention, the carbon tetrachloride will be in the liquid state and the temperature of treatment can be at ambient. In a further concept of the invention, the temperature will be in the approximate range of from about 0° to about 200° C., preferably from about 10° to about 100° C. while the carbon tetrachloride will be in the liquid state; at least the carbon tetrachloride will be predominately in the liquid state during the regeneration. Completely gaseous carbon tetrachloride can be used but this is not now preferred.

I have discovered that carbon tetrachloride, unlike a number of other tested solvents, will permit repeated regenerations and reuse of a ruthenium-containing hydrogenation catalyst to obtain good yields of a product. Indeed, there has been obtained on regeneration according to the invention, an activity of catalyst exceeding its original activity.

It is an object of this invention to provide a process for the regeneration of a hydrogenation catalyst. It is another object of the invention to provide a process for the regeneration of a ruthenium-containing catalyst, for example, a hydrogenation catalyst which has been used to effect a hydrogenation, as herein described.

Other aspects, concepts, objects, and the several advantages of the invention are apparent from a study of this disclosure and the appended claims.

According to the present invention, a used, supported ruthenium catalyst which has been partially deactivated by use in a hydrogenation process, is regenerated by contacting the catalyst with carbon tetrachloride under regeneration conditions as herein described.

Thus, according to the invention, there is provided a process in which a ruthenium catalyst which has been used in a catalytic hydrogenation and therein at least partially deactivated, is regenerated by contact with carbon tetrachloride whereupon the catalyst can be reused in the same or a different hydrogenation reaction.

Supported ruthenium catalysts are known to be useful for catalyzing hydrogenation reactions. However, for commercial use it is important that the catalyst be capable of regeneration to allow repeated use of the expensive metal. Supported ruthenium catalysts have been found to be difficult to regenerate. Although the reason for this regeneration problem is not firmly established, it has been suggested that during the attempted regeneration the ruthenium metal migrates to form large crystallites with a reduced metal surface area and a reduced activity.

The ruthenium catalysts suitable for regeneration by the process of this invention are supported ruthenium catalysts. The catalyst support or carrier can be any solid support which does not deleteriously affect the catalytic process. Examples of supports include carbon, kieselguhr, silica, alumina, silica-alumina, calcium carbonate, barium carbonate, pumice, clays, and the like, and mixtures thereof. For reasons of economics, stability, and inertness, the presently preferred support is alumina. The support can be in the form of spheres, pellets, extrudates, tablets, granules, and the like, and mixtures thereof. The size of the catalyst support will be any size suitable for the particular catalytic reaction and equipment.

The amount of ruthenium present on the support will vary somewhat depending on the nature of the groups being hydrogenated. In general, the supported ruthenium catalyst will contain ruthenium in the range from about 0.01 to about 50 weight percent and preferably in the range of about 0.1 to about 20 weight percent, based on the weight of the support.

The supported ruthenium catalyst can be prepared by any of the methods well-known in the art. The ruthenium catalyst can be added to the support as the finely divided elemental ruthenium or compounds of ruthenium which are reducible by hydrogen to finely divided elemental ruthenium. Suitable reducible compounds include ruthenium oxide, ruthenium chloride, ruthenium nitrate, ruthenium acetate, ruthenium carbonate, ruthenium hydroxide, and the like. The ruthenium catalyst can be added to the support by any of a variety of methods. For example, the supported catalysts can be prepared by dry mixing the components or by impregnating the support with a solution or a dispersion of ruthenium in elemental form or in the form of reducible compounds thereof. The supported catalyst can be pretreated with hydrogen to reduce the compounds, or such reduction can be achieved in the hydrogenation reactor. Examples of supported catalysts include 0.5 percent ruthenium on alumina, 1 percent ruthenium on alumina, 10 percent ruthenium on alumina, 5 percent ruthenium on carbon, 15 percent ruthenium on silica, 3 percent ruthenium on kieselguhr, and 6 percent ruthenium on calcium carbonate. Promoters or activators, such as chromium, palladium, silver, manganese, and the like can be present in the supported catalyst if desired.

The catalyst regeneration process of this invention is carried out by contacting the supported ruthenium catalyst with carbon tetrachloride under regenerating conditions.

As noted, suitable regenerating temperatures will generally be within the broad range of from about 0° to about 200° C., preferably from about 10° to about 100° C. While the carbon tetrachloride can be in a liquid state or a gaseous state during the regeneration, it is currently preferred that the carbon tetrachloride be predominantly in the liquid state during the regeneration. Regeneration pressures will be broadly from about atmospheric to about 1000 psig (689.4 kiloPascals gauge-kPa), preferably from atmospheric to about 500 psig (345 kPa). The time required for the catalyst regeneration will depend on the particular temperature and pressure utilized, but will be generally from a few minutes to about 48 hours. For an efficient and economical operation, the time for regeneration is preferably from about 1 hour to about 24 hours.

The amount of carbon tetrachloride utilized in the regeneration procedure can be expressed in terms of a volume ratio of the carbon tetrachloride to the supported ruthenium catalyst (including support). The volume ratio of carbon tetrachloride to catalyst will be broadly from about 0.5/1 to about 1000/1 and preferably will be from about 1/1 to about 100/1. Although it is generally preferred that the carbon tetrachloride employed in the catalyst regeneration be relatively pure, e.g., greater than about 95 weight percent carbon tetrachloride, other materials that do not adversely affect the catalyst regeneration, e.g., chloroform, methylene chloride, tetrachloroethane, and the like, can be present in quantities of up to as much as about 25 weight percent.

At the conclusion of the catalyst regeneration treatment, the catalyst and the carbon tetrachloride are separated using any suitable technique such as decanting, draining, filtering, and the like. The separated catalyst is preferably treated by contact with a flowing inert gas, e.g., nitrogen, helium, and the like, or by heating to remove remaining carbon tetrachloride.

It is currently preferred that the regenerated ruthenium catalyst be reduced in the presence of hydrogen at a temperature of about 100° C. to about 600° C. for a time of a few minutes to about 10 hours.

Since the carbon tetrachloride employed in the catalyst regeneration treatment will accumulate organic material during the regeneration, the carbon tetrachloride is preferably purified between regenerations by any suitable technique, such as distillation.

Although not currently preferred, a supported ruthenium catalyst can be pretreated before use with carbon tetrachloride to improve catalyst activity.

The supported ruthenium catalysts that are regenerated by the process of the present invention are useful in catalytic hydrogenation reactions. Groups which can be hydrogenated include acetylenic, olefinic, nitrile, carbonyl, aromatic, and the like, and mixtures thereof.

Specific examples of hydrogenation reactions include the conversion of acetylene to ethane, propene to propane, cyclohexane to cyclohexane, adiponitrile to hexamethylenediamine, acrylonitrile to 1-propylamine, cyclohexanone to cyclohexyl alcohol, butyraldehyde to 1-butanol, benzene to cyclohexane, and toluene to methylcyclohexane.

The currently preferred hydrogenation substrate for use with the supported ruthenium catalyst are branched-chain unsaturated aliphatic dinitriles of the formula:

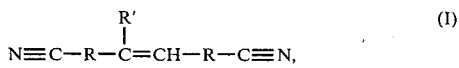
(I)

wherein each R is independently selected from the group consisting of an alkylene radical and an alkylidene radical and R' is an alkyl radical. Each R will generally have from one to fifteen carbon atoms, preferably from one to six, and more preferably from one to three carbon atoms. R' will generally have from one to 15 carbon atoms, preferably from one to six carbon atoms, and more preferably from one to three carbon atoms. In general, the unsaturated dinitrile reactant of formula (I) will contain from seven to 30 carbon atoms, preferably from eight to 16 carbon atoms, and more preferably from nine to 12 carbon atoms.

Representative of unsaturated reactant species of formula (I) include such compounds as 4-methyl-3-hexenedinitrile, 4-ethyl-3-hexenedinitrile, 5-methyl-4-nonenedinitrile, 5-ethyl-4-decenedinitrile, 7-methyl-6-tridecenedinitrile, 7-methyl-6-pentadecenedinitrile, 12-methyl-12-tetracosenedinitrile, 10-hexyl-9-tetracosenedinitrile, 2,3-dimethyl-3-hexenedinitrile, 2,4,6-trimethyl-3-heptenedinitrile, 4-ethyl-6,7-dimethyl-3-octenedinitrile, 2,4,6-triethyl-3-octenedinitrile, 2-ethyl-4,6-dipropyl-3-octenedinitrile, 2-methyl-4,6,8,10-tetrapropyl-3-dodecenedinitrile, 2,4,7,9,11,13,15-heptaethyl-6-hexadecenedinitrile, and mixtures thereof.

If desired, other unsaturated dinitrile reactants can be present and effectively hydrogenated during the hydrogenation of the unsaturated dinitriles of formula (I). Thus, in addition to the unsaturated dinitrile reactants of formula (I), the dinitrile feedstock can contain one or more unsaturated dinitrile reactants of the formula:

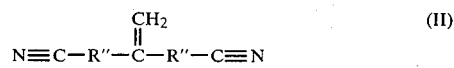
(II)

wherein each R'' is independently selected from the group consisting of an alkylene radical and an alkylidene radical. In general, each R'' will have from one to 15 carbon atoms, preferably from one to seven carbon atoms, and more preferably from one to four carbon atoms. The dinitriles of formula (II) will generally contain from six to 30 carbon atoms, preferably from eight to 16 carbon atoms, and more preferably from nine to 12 carbon atoms. Representative unsaturated dinitrile reactants of formula (II) include such compounds as 3-methylenehexanedinitrile, 4-methyleneheptanedinitrile, 5-methylenenonanedinitrile, 6-methyleneundecanedinitrile, 7-methylenetridecanedinitrile, 8-methylenepetadecanedinitrile, 12-methylenetetracosanedinitrile, 15-methylenenonacosanedinitrile, 2-methyl-3-methylenepentanedinitrile, 2,4-dimethyl-3-methylenepentanedinitrile, 2-methyl-4-methyleneoctanedinitrile, 2-methyl-7-ethyl-4-methyleneoctanedinitrile, 2,4,8-trimethyl-6-methylenedodecanedinitrile, 2,4,8,10-tetrapropyl-6-methylenedocecanedinitrile, 2,26-dimethyl-14-methyleneheptacosanedinitrile, and mixtures thereof.

Unsaturated dinitriles having a structure other than that of formulas (I) and (II) can be present during the hydrogenation reaction, if desired. Similarly, other compounds which may be found in the feed source of the dinitriles of formulas (I) and (II) can be present so long as such additional compounds do not significantly adversely affect the hydrogenation of the dinitriles of formulas (I) and (II). Where other dinitriles are present in the feedstock, the dinitriles of formula (I) will generally constitute at least 0.1 weight percent of the total dinitriles.

A presently most preferred branched-chain unsaturated aliphatic dinitrile feedstock is the dinitrile reaction product mixture obtained by the reaction of isobutylene and acrylonitrile. This dinitrile reaction product mixture generally comprises 5-methyl-4-nonenedinitrile, 2,4-dimethyl-4-octenedinitrile, 2,4-dimethyl-3-octenedinitrile, 2,4,6-trimethyl-4-heptenedinitrile, 5-methylenenonanedinitrile, 2-methyl-4-methyleneoctanedinitrile, and 2,6-dimethyl-4-methyleneheptanedinitrile. The first four named compounds in this mixture are of the type of formula (I), while the last three named compounds in this mixture are of the type of formula (II). The weight ratio of the dinitriles of formula (I) to the dinitriles of formula (II) in this mixture is generally in the range of about 10:1 to about 1:10.

The catalytic hydrogenation of the unsaturated dinitrile reactant of formula (I) results primarily in the formation of saturated diamine reaction products having the formula:

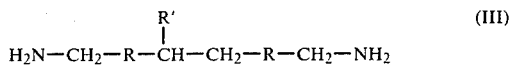

wherein R and R' are as previously defined. The catalytic hydrogenation of an unsaturated dinitrile reactant of formula (II) results primarily in the formulation of saturated diamine reaction products having the formula:

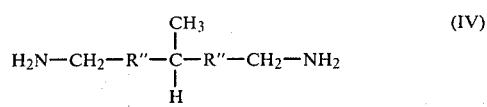

wherein R'' is as previously defined.

The reaction condition used for catalytic hydrogenation reactions with the supported ruthenium catalyst will generally be those conditions known in the art to provide the desired reaction. When the supported ruthenium catalyst is to be used for the hydrogenation of the presently preferred substrates—branched chain unsaturated aliphatic dinitriles—the following reaction conditions are suitable.

The hydrogenation temperature will generally be in the range from about 30° to about 250° C., preferably from about 70° to about 200° C. Hydrogen pressures employed will be broadly from about 100 to about 5000 psig (689 to 34470 kiloPascals gauge-kPa), preferably from about 500 to about 3000 psig (3447 to 20682 kPa).

Any time interval suited for the catalytic hydrogenation of branched-chain unsaturated aliphatic dinitriles can be employed. However, time intervals economically attractive to the process are generally within the range of about 15 minutes to about 5 hours for a batch hydrogenation process. A reaction time in the range of about 1 to about 3 hours is presently preferred. The catalytic hydrogenation of unsaturated dinitriles can be carried out as a continuous process at any suitable liquid hourly space velocity (LHSV). However, the liquid hourly space velocity rates will generally be within the range of about 0.1 to about 20, more preferably from about 0.5 to about 10, volumes of unsaturated dinitrile reactant plus diluent and ammonia per volume of catalyst (including the volume of the catalyst support).

Diluents employed in the hydrogenation of branched-chain unsaturated aliphatic dinitriles are usually selected from aliphatic tertiary alcohols, acyclic and cyclic ethers, and saturated hydrocarbons. Examples include 2-methyl-2-propanol, 2-methyl-2-butanol, dipropyl ether, 1,4-dioxane, dodecane, cyclododecane, and the like, and mixtures thereof. To facilitate handling of the reaction mixtures, the weight ratio of unsaturated dinitrile reactants to diluent charged to the reaction zone is generally within the weight ratio range of about 0.001:100 to about 15:100, and is preferably in the range of about 0.1:100 to about 12:100.

A secondary amine formation suppressant, preferably ammonia, is employed as a means of suppressing undesirable side reactions such as the formation of secondary and tertiary amines. Any amount of secondary amine formation suppressant can be employed which is effective in deterring or reducing undesirable side reactions. In general, the mole ratio of secondary amine formation suppressant to cyano group (there being two cyano groups in each unsaturated dinitrile) will be in the range of about 1:1 to about 25:1, and preferably will be in the range of about 7:1 to about 15:1.

Recovery of the desired end product from the hydrogenation of branched-chain unsaturated dinitriles, the branched-chain saturated aliphatic diamines, as well as any resulting reaction byproducts, any unconsumed reactants, ammonia, hydrogen, and/or diluents can be carried out by any conventional separation means. In general, at the conclusion of the catalytic hydrogenation process in a batch process, the reaction zone effluent is cooled and depressurized with the recovery, if desired, of any ammonia or diluent which is vented from the reaction zone effluent during the depressurization operation. The ammonia or diluent can be returned or recycled to the hydrogenation zone if desired. The reaction products can be separated from the catalyst by conventional filtration means. The filtrate containing the saturated diamines can be conveniently separated from any reaction byproducts or any diluent remaining in the filtrate by any conventional fractional distillation.

In a continuous process, the reactor effluent is depressured and the diluent and ammonia removed by distillation. The recovered diluent and ammonia can be recycled to the hydrogenation zone, if desired. The saturated diamines can be separated from any reaction byproducts or any remaining diluent by any conventional fractional distillation.

The saturated diamine products obtained by the hydrogenation of unsaturated dinitriles are useful in the preparation of polymers. Of particular interest are the polyamides. The terephthalamide polymers have been found to be of value for the production of fibers and engineering plastics.

Hexamethylenediamine, obtained by the hydrogenation of adiponitrile, is useful as a component of nylon 6,6. Cyclohexanol, obtained from cyclohexanone by hydrogenation, has been used as a solvent and in the manufacture of insecticides. The hydrogenation of benzene yields cyclohexane, which is useful as a solvent and in the preparation of adipic acid (a component of nylon 6,6).

EXAMPLES

The starting material in each of the runs in the examples is a mixture of olefinically unsaturated dinitriles prepared by the reaction of isobutylene and acrylonitrile. This reaction mixture contains about 52 weight percent 5-methylenenonanedinitrile, about 35 weight percent 5-methyl-4-nonenedinitrile, about 12 weight percent of the combination of 2,4-dimethyl-4-octenedinitrile, 2-methyl-4-methyleneoctanedinitrile, and 2,4-dimethyl-3-octenedinitrile, and about 1 weight percent of the combination of 2,6-dimethyl-4-methyleneheptanedinitrile and 2,4,6-trimethyl-3-heptenedinitrile. For simplicity, the above described reaction mixture will be called diadduct. Hydrogenation of both the olefinic and the nitrile unsaturation of diadduct yields a mixture of saturated diamines.

In each hydrogenation run, a 0.5" (12.7 mm) diameter×30" (508 mm) length continuous reaction fitted with steam heating system and temperature recorder was charged with 20 g of the supported catalyst, flushed with nitrogen, flushed with hydrogen at a rate of 1 liter per minute and heated to 140° C. A mixture containing diadduct, 2-methyl-2-propanol, and ammonia in a weight ratio of 1/8/1 was fed to the reactor at a LHSV of about 6. The reactor conditions during the hydrogenation runs were 1500 psig (10.3 MPa) pressure, 140° C., and 1 liter per minute hydrogen flow.

Samples were collected from the reactor effluent after 4 hours of run time and after 19 hours of run time and were analyzed by vapor phase chromatography after removal of the 2-methyl-2-propanol and ammonia under reduced pressure. The results of each run are expressed as a weight percent saturated diamines present in the product mixture at the indicated time in the run with the percentage based on the product weight after removal of the 2-methyl-2-propanol and ammonia.

The catalysts in Examples II and III were prepared by impregnating an 8×14 mesh granular gamma-alumina with $RuCl_3$ in water, drying under reduced pressure, and reducing for 3 hours in the presence of hydrogen at 400° C. (Example II) or 500° C. (Example III). The amount of elemental ruthenium on the support was 0.5 weight percent. In Examples I, IV, and V, the catalyst was a commercial catalyst containing 0.5 weight percent ruthenium on a gamma-alumina (1/16" extrudate). The percentages are calculated on the basis of the support weight. The solvents used in the examples were commercial materials which were not purified further.

The catalyst regenerations using solvents were carried out by contacting the used catalyst with the solvent at about 25° C. and atmospheric pressure for 2 or 12 hours. The solvent was decanted from the catalyst and the catalyst was placed in the reactor. Nitrogen gas was passed through the reactor to remove residual solvent and the catalyst was reduced in the presence of hydrogen for 3 hours at 400° or 500° C.

EXAMPLE I

A control run was carried out to demonstrate the results of a conventional thermal oxidative treatment for the attempted regeneration of a ruthenium catalyst. A fresh Ru on alumina catalyst was utilized in run 1 in the hydrogenation of diadduct for 19 hours. The amount of saturated diamines present in the product mixture after 4 hours of run time was 76% and after 19 hours was 56%. The catalyst was regenerated by heating in nitrogen at 300° C. for 3 hours, in a nitrogen-oxygen mixture (1 volume % $O_2$) at 300° C. for 2 hours, and then in another nitrogen-oxygen mixture (2 volume % $O_2$) at 300° C. for 5 hours. Following this regeneration procedure, the catalyst was reduced in the presence of hydrogen at 400° C. for 3 hours.

The regenerated catalyst was utilized in run 2 in another hydrogenation of diadduct. The amount of saturated diamines present after 4 hours was 37% and after 19 hours was below 25%. These results show that a conventional thermal oxidative regeneration procedure is ineffective for the regeneration of a supported Ru catalyst.

EXAMPLE II

A series of runs was carried out to demonstrate the regeneration process of the present invention. In each run, the continuous hydrogenation of diadduct was carried out for a total of 19 hours over a Ru on alumina catalyst. A fresh catalyst was used in run 3 and was then used in each of the following runs with a carbon tetrachloride treatment between each run. The carbon tetrachloride regenerations were carried out at about 25° C. for 2 or 12 hours. The treated catalyst was dried with nitrogen and reduced with hydrogen at 400° C. for 3 hours. Table I presents the results of these runs.

TABLE I

| Run No. | Catalyst | Saturated Diamines, Wt. %[a] | |
|---|---|---|---|
| | | After 4 hours | After 19 hours |
| 3 | Fresh Catalyst | 66 | 45 |
| 4 | $CCl_4$ Regenerated - 2 hrs. | 63 | 45 |
| 5 | $CCl_4$ Regenerated - 12 hrs. | 68 | 61 |
| 6 | $CCl_4$ Regenerated - 12 hrs. | 78 | 72 |
| 7 | $CCl_4$ Regenerated - 12 hrs. | 78 | 68 |
| 8 | $CCl_4$ Regenerated - 12 hrs. | 81 | 61 |
| 9 | $CCl_4$ Regenerated - 12 hrs. | 76 | 51 |

[a]Weight percent saturated diamines present in the product mixture after removal of the 2-methyl-2-propanol and ammonia.

The results in Table I demonstrate the process of the present invention for the regeneration of a used, supported ruthenium catalyst by contacting the catalyst with carbon tetrachloride. The yields of saturated diamines are higher in the later runs than in the initial runs.

EXAMPLE III

Another series of runs was carried out to demonstrate the process of the present invention. A fresh catalyst was used in run 10 and was then used in runs 11 and 12 with a carbon tetrachloride treatment between each run. The carbon tetrachloride regenerations were carried out at about 25° C. for 12 hours. The regenerated catalysts were dried with nitrogen and reduced with hydrogen at 500° C. (run 11) or 400° C. (run 12). Table II presents the results of these runs.

TABLE II

| Run No. | Catalyst | Saturated Diamines, Wt. %[a] | |
|---|---|---|---|
| | | After 4 hours | After 19 hours |
| 10 | Fresh Catalyst | 91 | 73 |
| 11 | $CCl_4$ Regenerated | 88 | 71 |
| 12 | $CCl_4$ Regenerated | 77 | 54 |

[a]See footnote [a] in Table I.

These results show that the carbon tetrachloride regeneration treatment of the present invention gives higher yields of the saturated diamines than the thermal oxidative regeneration in Example I.

EXAMPLE IV

Several control runs were carried out to show that chlorinated hydrocarbons other than carbon tetrachloride are less effective than carbon tetrachloride for the regeneration of supported ruthenium catalysts. A fresh catalyst was used in run 13 and the resulting catalyst was treated with 1,1,1-trichloroethane at about 25° C. for 12 hours. The treated catalyst was dried with nitrogen, reduced at 400° C. for 3 hours, and used in run 14.

A fresh catalyst was used in run 15 and the resulting catalyst was treated with methylene chloride at about 25° C. for 12 hours. The treated catalyst was dried with nitrogen, reduced at 500° C. for 3 hours, and used in run 16. The results of these runs are presented in Table III.

TABLE III

| Run No. | Catalyst | Saturated Diamines, Wt. %[a] | |
| --- | --- | --- | --- |
| | | After 4 hours | After 19 hours |
| 13 | Fresh Catalyst | 80 | 53 |
| 14 | $CH_3CCl_3$ Regenerated | 64 | 39 |
| 15 | Fresh Catalyst | 78 | 53 |
| 16 | $CH_2Cl_2$ Regenerated | 49 | <25 |

[a]See footnote [a] in Table I.

These results show that other chlorinated materials are much less effective than carbon tetrachloride for the regeneration of supported ruthenium catalysts.

EXAMPLE V

Several more control runs were carried out using other solvents in attempted ruthenium catalyst regenerations. Three pairs of runs were carried out in which the first run in a pair used a fresh, supported ruthenium catalyst. At the conclusion of the first run, the used catalyst was contacted with a solvent (methanol, toluene, or acetone) at about 25° C. for 12 hours, dried with nitrogen, and reduced with hydrogen at 500° C. for 3 hours. The results of these runs are presented in Table IV.

TABLE IV

| Run No. | Catalyst | Saturated Diamines, Wt. %[a] | |
| --- | --- | --- | --- |
| | | After 4 hours | After 19 hours |
| 17 | Fresh Catalyst | 85 | 67 |
| 18 | Methanol Treated | 61 | 46 |
| 19 | Fresh Catalyst | 80 | 60 |
| 20 | Toluene Treated | 62 | 45 |
| 21 | Fresh Catalyst | 80 | 58 |
| 22 | Acetone Treated | 34 | <25 |

[a]See footnote [a] of Table I.

These results show that methanol, toluene, and acetone are less effective than carbon tetrachloride for the regeneration of used, supported ruthenium catalysts.

Reasonable variation and modification are possible within the scope of the foregoing disclosure and the appended claims to the invention the essence of which is that a used or at least partially deactivated ruthenium-containing hydrogenation catalyst can be regenerated by treatment with carbon tetrachloride substantially as described herein.

I claim:

1. A regeneration process comprising contacting under regeneration conditions an at least partially deactivated ruthenium-containing catalyst with a regeneration agent consisting essentially of carbon tetrachloride at least partially in the liquid phase; wherein said catalyst has been used to hydrogenate a branched-chain unsaturated aliphatic dinitrile.

2. A regeneration process comprising contacting an at least partially deactivated ruthenium-containing catalyst with a regeneration agent consisting essentially of carbon tetrachloride; wherein said catalyst has been used to hydrogenate a branched-chain unsaturated aliphatic dinitrile; and wherein the temperature is in the range of from about 10° to about 100° C. and the pressure is in the range of from about atmospheric to about 1000 psig.

3. A regeneration process according to claim 1 wherein said carbon tetrachloride is contacted with said catalyst under conditions maintaining a predominant portion of the carbon tetrachloride in the liquid phase.

4. A process according to claim 1 wherein the carbon tetrachloride is substantially in the gaseous phase.

5. A process according to claim 1 or 2 wherein the temperature is within the ambient range.

6. A process according to claim 1 or 2 wherein said catalyst and said carbon tetrachloride are separated at the conclusion of the regeneration treatment.

7. A process according to claim 6 wherein the separated catalyst is treated by contact with a flowing inert gas to remove remaining carbon tetrachloride.

8. A process according to claim 7 wherein said inert gas is nitrogen.

9. A process according to claim 7 wherein said inert gas is helium.

10. A process according to claim 6 wherein the separated catalyst is heated to remove remaining carbon tetrachloride.

11. A process according to claim 7 wherein the separated catalyst is reduced.

12. A process according to claim 10 wherein the separated catalyst is reduced.

13. A process according to claim 1 or 2 wheren said carbon tetrachloride is decanted from said catalyst, said catalyst is placed in a reactor, nitrogen gas is passed through said reactor to removal residual carbon tetrachloride from said catalyst, and said catalyst is reduced.

* * * * *